United States Patent [19]

Allen

[11] Patent Number: 5,159,049
[45] Date of Patent: Oct. 27, 1992

[54] METHOD FOR STABILIZING POLYACRYLAMIDE GELS

[76] Inventor: Robert C. Allen, 501 Palm Blvd., Isle of Palms, S.C. 29451

[21] Appl. No.: 688,296

[22] Filed: Apr. 22, 1991

[51] Int. Cl.$^5$ ............................................. C08L 5/00
[52] U.S. Cl. ...................................... 524/56; 524/57; 524/58; 525/54.2
[58] Field of Search ........................... 524/56, 57, 58; 525/54.2; 527/314

[56] References Cited

U.S. PATENT DOCUMENTS

| | | | |
|---|---|---|---|
| 3,875,044 | 4/1975 | Renn et al. | 204/299 |
| 4,006,069 | 2/1977 | Hiratsuka et al. | 204/180 |
| 4,189,370 | 2/1980 | Boschetti | 204/299 R |
| 4,746,551 | 5/1988 | Allen et al. | 427/389.7 |

FOREIGN PATENT DOCUMENTS

0189169 10/1984 Japan ...................................... 524/56

OTHER PUBLICATIONS

Allen et al., "Rehydratable Gels: A Potential Reference Standard Support for Electrophoresing PCR-Amplified DNA" *Biotechnology*, 8:1288 (1990).
Frey et al., "Preparation of Rehydratable Polyacrylamide Gels and their Application in Ultrathin-Layer Isoelectric Focusing" *Electrophresis*, vol. 7, pp. 28–40 (1986).
Gelfi et al., "Swelling Kinetics of Immobiline Gels for Isoelectric Focusing" *Electrophoresis*, vol. 5, pp. 257 and 262.
Allen et al., "Enzyme and Antibody Detection Following Isoelectric Focusing on Ultrathin-Layer Rehydrated Polyacrylamide Gels" *Acta Histochem. Cytochem.*, vol. 19, No. 5, pp. 637–645.
Allen et al., "Tailoring DNA Resolution in Polyacrylamide Gels with Electrochemistry and Pulsed Constant Power" *Electrophoresis* '89, p. 91 (1989).

*Primary Examiner*—Paul R. Michl
*Assistant Examiner*—LaVonda R. DeWitt
*Attorney, Agent, or Firm*—Rothwell, Figg, Ernst & Kurz

[57] ABSTRACT

A method for preparing stabilized, rehydratable polyacrylamide gels, wherein the stabilizers employed include substituted monosaccharides where the hydroxyl group of the carbon 1 is substituted with a non-charged group comprising an α-methyl group or an oligosaccharide having from 2 to about 8 repeating units which can be the same or different. These rehydratable gels can be stored for extended periods of time at ambient temperatures, and can be rehydrated without loss of structural or functional integrity to be used for electrophoretic separation of proteins and nucleic acids.

26 Claims, 1 Drawing Sheet

METHOD FOR STABILIZING POLYACRYLAMIDE GELS

BACKGROUND OF THE INVENTION

The present invention relates to an improved method of stabilizing polyacrylamide gels of various types. More specifically, this invention relates to a method for stabilizing rehydratable polyacrylamide gels with substituted monosaccharides or oligosaccharides. These rehydratable polyacrylamide gels can be stored for extended periods of time at ambient temperatures, and can be rehydrated without loss of structural or functional integrity to be used for electrophoretic separation of proteins and nucleic acids.

Polyacrylamide gels are used as a support matrix for the electrophoretic separation of proteins, double-stranded DNA, and single stranded RNA. Typically, polyacrylamide gels are prepared individually just prior to use as homogeneous or gradient pore size gels. Precast wet gels bonded to polyester sheets can be obtained commercially. These precast polyacrylamide gels must be stored in sealed containers to prevent evaporation.

Rehydratable polyacrylamide gels bonded to a polyester support have been disclosed in the art (see, for example, U.S. Pat. No. 4,746,551, issued to Allen, et al., 1988). The patent teaches that the rehydratable polyacrylamide gels can be stabilized with polyols, polymeric alcohols, polyamines or high molecular weight polysaccharides such as dextran. The protective action of these stabilizers appears to occur on the surface of the polyacrylamide gels. These stabilizers are too large to penetrate the matrix and pores of the polyacrylamide gel to any great degree, i.e., not more than about 3% of the polysaccharide stabilizes the gel to control residual wetness.

It has been found to be desirable to store these gels in containers, otherwise the pore spaces may collapse from loss of residual moisture with resultant shrinking of the gel when the relative humidity falls below 70%. This can cause curling of the polyester backing and eventual peeling of the gel from the backing. Also, as humidity rises, the surface of the gels can hydrate, and the gels can become stuck to the packing material with surface destruction when the gels are peeled away for use. Thus, storage can be a problem, and care must be taken when storing the rehydratable gels.

Other methods at attempting to prepare and/or stabilize gels for electrophoretic use can be found in U.S. Pat. Nos. 3,875,044, 4,006,069, and 4,189,370. U.S. Pat. No. 3,875,044, issued to Renn et al., discloses hydratable gel sheets and methods for preparing them. The gel sheets can be prepared from agar, agarose or gelling carrageenan. The gel is joined to a support backing by drying the gel sheet to the support backing such that a bond is formed between the two components so that the gel sheet does not slide from the support backing. Thus, a relatively firm and rigid structure can be formed which maintains its shape and dimensions. The hydratable gels then can be used in immunodiffusion, continuous zone electrophoresis (CZE), or chromatographic procedures. The gels disclosed in this patent are limited to CZE as opposed to other forms of electrophoresis because there is considerable electroendosmotic flow from the materials which comprise the gels, i.e., agar, agarose and carrageenan. Also, because the pore sizes of the gels described in this patent are relatively large, separation of small DNA and RNA is limited, and many macromolecules will migrate with the boundaries, thus preventing multizonal electrophoresis (MZE).

U.S. Pat. No. 4,006,069, issued to Hiratsuka et al., discloses an electrophoretic support made of a cellulosic material such as cellulose acetate. The pores of the support are infiltrated with a polymeric gel membrane composed of polyacrylamide or starch or agar. The polymeric gel membrane is tough and reportedly does not break during use or substantially shrink upon drying after electrophoresis (CZE). However, cellulose acetate has charged pores which cause electroendosmotic flow; thus, isoelectric focusing is impossible with these gels. The cellulose acetate also prevents silver staining for proteins and nucleic acids. Further, the large pore sizes of these gels prevents the separation of small DNA and RNA as well as MZE electrophoresis.

U.S. Pat. No. 4,189,370, issued to Boschetti, discloses a process for preparing plates made of a gel-polymer for the electrophoretic separation of serif or plasmatic lipoproteins. The gel-polymer can be made by radical polymerization of N-methylol-acrylamide and a bifunctional allylic or acrylic cross-linking agent. The plates described herein can be treated with a mixture of a simple sugar, a diol or a triol and a carboxylic polysaccharide, previously treated by a reducing agent, may be air-dried, then rehydrated to regain its original characteristics. These gels have several disadvantages. Because the gel is made with a substituted polyacrylamide which contains a free charge group, electroendosmotic flow characteristics are imparted to the gel, thereby making it unsuitable for the separation of macromolecules by isoelectric focusing. In addition, the low molecular weight polyols he discloses, such as glycerol and ethylene glycol, can intersect with nucleic acids and proteins, thereby altering their mobility in moving boundary systems. They thus are unsuitable as preservatives, as discussed in more detail below.

Attempts have been made to improve the stabilization of rehydratable gels using polyhydroxy alcohols, or linear sugar alcohols typically employed as matrix modifiers in gels employed in the separation of double-stranded DNA. Allen, et al., "Rehydratable Gels: A Potential Reference Standard Support For Electrophoresing PCR-Amplified DNA" *Biotechnology*, 8:1288 (1990), and Allen, et al., "Tailoring DNA Resolution in Polyacrylamide Gels with Electrochemistry and Pulsed Constant Power" *Electrophoresis* ,'89, page 91 (1989). These compounds can be used to alter the mobility and resolution of nucleic acids in a given pore size gel. This characteristic renders them unsuitable for the stabilization of an inert or empty gel. These matrix modifiers, in particular glycerol, tend to make the gel surface sticky and will glue to the protective film covering the gels during storage. Frey, et al., "Preparation of Rehydratable Polyacrylamide Gels and their Application in Ultrathin-Layer Isoelectric Focusing" *Electrochoresis* 1986, vol. 7, pp. 28–40 (1986). Preferably, glycerol is removed from rehydratable gels by washing with distilled water prior to drying the gels for storage. Gelfi, et al., "Swelling Kinetics of Immobiline Gels for Isoelectric Focusing" *Electrophoresis*, vol 5, pp. 257-262 (1984).

In addition to glycerol, the sugar alcohols used as matrix modifiers, such as sorbitol and mannitol, also have been found unsuitable as preservatives. Polyols, such as ethylene glycol and glycerol and the sugar alcohols, such as sorbitol and mannitol, interact with nucleic acids, altering mobility in high resolution moving boundary electrophoresis. In addition, glycerol recently has been shown to interact not only with nucleic acids, but also with proteins and enzymes. For example, the mobility of erythrocyte acid phosphatase is altered in a manner such that two of the isotypes or isoforms are no longer distinguishable in its presence. Allen, et al., "Enzyme and Antibody Detection Following Isoelectric Focusing on Ultrathin-Layer Rehydrated Polyacrylamide Gels" *Acta Histochem. Cytochem.*, Vol. 19, No. 5, pp. 637-645 (1986).

Therefore, there exists a need for a method of stabilizing rehydratable polyacrylamide gels such that the integrity of the gel is maintained for electrophoretic separation of proteins, enzymes, DNA, RNA and the like throughout storage at ambient temperatures and upon rehydration prior to use, and the stabilizers employed do not significantly interact with the substrates to be separated.

SUMMARY OF THE INVENTION

In accordance with the present invention, a method for stabilizing rehydratable polyacrylamide gels used for the electrophoretic separation of proteins, enzymes, DNA, RNA and the like comprises polymerizing acrylamide monomers and one or more cross-linking agents to form a wet gel matrix; removing residual components of polymerization from the wet gel; incorporating a stabilizing amount of one or more substituted monosaccharides, oligosaccharides, or combinations thereof within the wet gel matrix; and then drying the wet gel to form a stabilized dry gel.

DETAILED DESCRIPTION OF THE INVENTION

Figure 1:
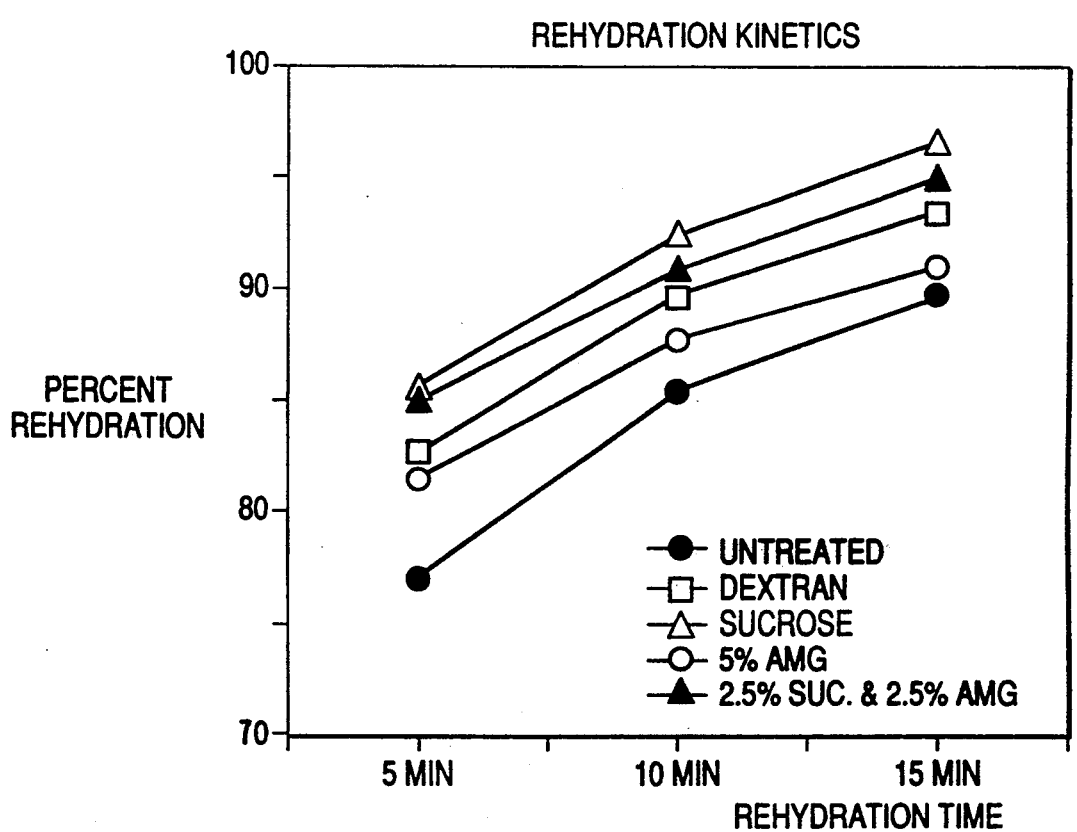
FIG. 1 illustrates percent rehydration versus time plot of the rehydration kinetics of five individual rehydratable polyacrylamide gels with different stabilizers.

In accordance with the present invention, monomers of acrylamide and one or more cross-linking agents are polymerized in accordance with conventional methods known to those of skill in the art to form a polyacrylamide gel having a matrix composed of polyacrylamide and one or more cross-linking agents and pores which traverse through the gel matrix. The polyacrylamide gel has a three dimensional lattice of long polyacrylamide chains which are connected at distinct intervals by the cross-linking agent.

The sizes of the pores can vary, and the pore size can be controlled by varying the total monomer concentration, i.e., the sum of the concentration of the acrylamide monomers and the concentration of the cross-linking agents. The effective pore size is the inverse function of the total monomer concentration. When the percent of the acrylamide monomer is increased and a low percent of cross-linker is maintained, the frequency of the polymeric chains increases, thereby reducing the pore size. This has been shown for gel concentrations of up to 40 and even 50% of acrylamide monomer and at 5% of the monomer concentration of cross-linking agent. As cross-linking is increased, a regular array of chains linked by cross-linker is formed, which at 5% cross-linker has maximum sieving properties, i.e., minimum pore size with a constant value of acrylamide monomer. The acrylamide monomer concentration typically can range from about 2.5% w/v to about 30% w/v of the total composition, with a preferred range from about 3.0% w/v to about 15% w/v for optimum sieving properties for electrophoretic separation of macromolecules, i.e., proteins, enzymes, and nucleic acid polymers. The amount of cross-linker monomer, generally ranges from about 2.0% w/v to about 35% w/v of the total composition with a preferred range of from about 2.5% w/v to about 6.0% w/v. The total monomer concentration, acrylamide monomer and cross-linker monomer, generally ranges from about 3.5% w/v to about 50% w/v, with a preferred range from about 5.5% w/v to about 21% w/v.

Cross-linking agents which can be used to practice this invention include conventional cross-linking agents employed in the art. Such cross-linking agents include, but are not limited to, methylene bisacrylamide, N,N 1-diallyltetradiamide, polyolefinic agarose (AcrylAid ®), N,N 1-(1,2-dihydroxyethylene) bisacrylamide, ethylene diacrylate, polyethylene glycol diacrylate, N,N,-bisacrylcystamine, and piperazine diacrylamide (PDA), or mixtures thereof. Preferred cross-linking agents are methylene bisacrylamide and PDA.

The acrylamide monomer and one or more cross-linking agents can be polymerized by any suitable method practiced in the art. For example, the acrylamide monomer and the cross-linking agents can be polymerized in aqueous solutions with free radical initiators such as t-butyl hydroperoxide, hydrogen peroxide, alkali metals and ammonium persulfates, chlorates, perchlorates, percarbonates, and the like. These polymerization reactions generally are conducted at temperatures of from about 35° C. to about 50° C. ranging in time from about 2 to about 4 hours. Alternatively, if high molecular weight polymers are desired, the polymerization reaction can be performed at lower temperatures, ranging from about 4° C. to about 35° C., by employing redox catalyst systems. The redox catalyst systems employed to practice this invention comprise oxidizing agents such as the initiators described above in combination with reducing agents such as thio sulfates, bisulfates, and dithiothreitol, and the like. The polymerization of acrylamide monomer and cross-linking agent also can be performed by photopolymerization in the presence of riboflavin or other photoactive polymerizing agents, or it can be performed in the absence of a chemical polymerizing agent by irradiation such as with high energy electron beams.

The unpolymerized reagents can be polymerized in any suitable reaction vessel employed in the art. Generally, the acrylamide monomer and cross-linking agent is applied to a mold in accordance with conventional methods practiced in the art including rolling on or sliding in closed systems, or in open systems under reduced oxygen tension such as in the presence of a nitrogen atmosphere. Capillary casting of the polyacrylamide gel can be performed between a hydrophilic polyester film affixed to a glass plate topped by a second plate whose gel-contiguous surface has been rendered hydrophobic by treatment with agents such as Repel Silane ® (2% dimethyldichlorosilane in 1,1,1-trichloroethane) from LKB, Rockville, Md., or rain'x ® (acidified ethanol/isopropanol) from Unelko, Scottsdale, Ariz., and separated by spacers of a defined thickness. The sides are allowed to remain exposed.

Although the unpolymerized reagents can be polymerized in a variety of polymerization vessels, preferably the reagents are poured onto support material which will covalently bond to the polymerized gel.

Examples of such support material include, but are not limited to, polyester or mylar films which have been rendered hydrophilic by treatment with agents such as Acrylaid ® or polyester sheets, mylar films or glass plates rendered hydrophilic with a silane compound such as Bind Silane ® (methacryloxy propyltrimethoxy silane). Commercially available supports include, for example, Gelfix ®, which is manufactured by Serva Fein Biochemicals of Heidelberg, Germany, and Gel-Bond-PAG ®, which is manufactured by Marine Colloids, Rockland, Me., a subsidiary of FMC Corp.

After the polymerization of the acrylamide monomer and cross-linking agent has been completed, forming a polyacrylamide gel, the residual components are removed from the gel. These residual components are unpolymerized acrylamide monomer, cross-linking agents, catalysts, and other unreacted components such as casting buffer and the like. Removing the residual components from the polyacrylamide gel reduces the conductance of the gel up to about seven-fold over similar gels which are conventionally prepared, especially when the gel comprises ampholytes for electrofocusing. This property of being an empty gel, i.e., a gel substantially free of charged components, allows higher voltage gradients to be used in the separation of proteins, enzymes, and nucleic acid polymers with reduced Joule heat. This shortens the separation time of the macromolecules to be separated with improved resolution in isoelectric focusing as well as in conventional moving boundary electrophoresis, particularly for double-stranded nucleic acids from 20 to 9000 base pairs and single-stranded RNA from 50 to 10,000 bases.

The gels can be washed by any suitable method used in the art such as equilibration equilibrium, ion exchange resins and the like. The preferred method of washing the gels to remove the residual components is by washing the gels against distilled water in an equilibration equilibrium process for a sufficient period of time to remove substantially all of the residual components. Generally, three washes of 20 minutes each are used with about 30 to about 40 volumes of water per volume of gel employed in each wash. About 99% or more of the residual reagents of polymerization can be removed by washing with distilled water. For example, in a 4% gel with a starting amount of acrylamide equal to about 0.52 gm, the acrylamide polymerizes with an efficiency of greater than about 99% leaving free at most about 1% or about 5.2 mg of unpolymerized acrylamide. A first washing with about 30 volumes of distilled water reduces the amount of unreacted acrylamide to about 0.173 mg. A second and third washing with 30 volumes of distilled water reduces the amount of unreacted acrylamide to about 5.7 $\mu$g, and then to about 190 ng, respectively. It is expected that a fourth washing with about 30 volumes of distilled water in the preservative step reduces the amount of unreacted acrylamide to about 6 picograms. It can be expected that about a 99.5% polymerization efficiency would have from about 3 to about 6 picograms (1 part in $6 \times 10^{12}$ or 1 in a trillion) of unreacted acrylamide in the finished gel.

After the residual components are removed from the polyacrylamide gel, a stabilizing amount of one or more substituted monosaccharides or oligosaccharides is incorporated into the pores of the polyacrylamide gel matrix. Although there is no intention to restrict the theory by which substituted monosaccharides or oligosaccharides stabilize polyacrylamide gels, it is contemplated that substituted monosaccharides or oligosaccharides fill in the void spaces within the pores of the gel matrix upon removal of moisture, thus maintaining the structural integrity of the gel. This is believed to prevent irreversible damage to the structure of the gel matrix on prolonged storage at ambient temperatures as well as highly elevated temperatures used in rapid drying and forced aging studies.

Substituted monosaccharides which are suitable in practicing this invention are substituted at the hydroxyl group at the 1 carbon position with an uncharged group such as a methyl group. Examples of substituted monosaccharides suitable for practicing this invention include $\alpha$-methyl-D-glucoside, $\alpha$-methyl-D-mannoside and the like.

In addition to the substituted monosaccharides disclosed above, oligosaccharides having from two to eight monosaccharide units which can be the same or different also can be used as stabilizers. One or more of the monosaccharide units optionally can carry a substituent, such as a methyl group on the 1 carbon position, if desired. Oligosaccharides which are not so substituted, however, are preferred, as they typically are much less costly. Examples of monosaccharides which can comprise an oligosaccharide include, but are not limited to, dextrose, mannose, galactose, fructose and ribose. Examples of oligosaccharides which are suitable for practicing this invention include sucrose, maltose, lactose, gentiobiose, raffinose, and melezitose, and the like. Preferred disaccharides include sucrose, maltose and lactose. The most preferred stabilizer is $\alpha$-methyl-D-glucoside alone or in combination with sucrose.

The substituted monosaccharides or oligosaccharides are added in amounts from about 2 to about 25% w/v of the polyacrylamide gel, but preferably from about 5 to about 10% w/v of the gel. The substituted monosaccharides and oligosaccharides employed in practicing this invention have the advantage that they do not interact with macromolecules, such as proteins, enzymes and nucleic acid polymers, during electrophoretic separation, thus permitting more accurate resolution of these macromolecules.

The substituted monosaccharides or oligosaccharides can be incorporated into the pores of the polyacrylamide gel by any suitable means practiced in the art. For example, the stabilizer can be incorporated into the gel by equilibration by placing the polyacrylamide gel into a solution of the stabilizer, and allowing the stabilizer to diffuse into the gel until equilibrium is reached between the concentration of the stabilizer inside the gel, and the concentration of the stabilizer outside the gel. Alternatively, the polyacrylamide gel can be partially dried before placing it in a solution containing one or more stabilizers. The polyacrylamide gels are partially dried at temperatures ranging from about 20° C. to about 120° C. for about 5 minutes to about 60 minutes depending on the temperature and method employed. Methods useful for partially drying the gels include those methods discussed below for completely drying the gels. Generally, once the gels are partially dried they are allowed to cool to room temperature before equilibration.

Polyacrylamide gels of the present invention can be molded into a variety of sizes and shapes, such as sheets, films, cylinders and columns etc. Polyacrylamide gels which are molded into sheets can be of conventional thickness of from about 30 to about 500 microns, but preferably from about 50 to about 500 microns in thickness.

The wet polyacrylamide gels comprising substituted monosaccharide or oligosaccharide stabilizers can be fully dried by various methods. For example, polyacrylamide gels can be air dried at from about 18° to about 25° C., or accelerated drying can be employed with infrared lamps in any conventional oven or microwave oven at temperatures ranging from about 50° to about 120° C. The time period over which the drying process occurs ranges from about 5 minutes to about 24 hours depending on the specific method employed. The dry rehydratable polyacrylamide gels of the present invention can be stored in a variety of containers, such as envelopes, boxes etc., since their surface is essentially glass-like.

The polyacrylamide gels of the present invention can be rehydrated with various solutions prior to the intended use of the gel. The specific solutions employed to rehydrate the gel depend upon the gels specific use. When polyacrylamide gels of the present invention are employed in continuous zone electrophoresis (also called single zone electrophoresis) for the separation of proteins or nucleic acids, rehydration solutions can include, but are not limited to, buffers such as 50 mM Tris-borate-EDTA at pH 8.0 for the separation of both proteins and nucleic acids, Tris-acetate for DNA and barbiturate-barbituric acid for the separation of proteins. Examples of solutions which can be employed in multizonal electrophoresis (MZE) include, but are not limited to, the solutions listed in Table I below.

TABLE I

| Leading Ion | Trailing Ion | Counter Ion | Valence Leading |
|---|---|---|---|
| Phosphate | Borate | Trizima Base | 3 |
| Citrate | Borate | Trizima Base | 3 |
| Sulfate | Borate | Trizima Base | 2 |
| Sulfate | Glycine | Trizima Base | 2 |
| Chloride | Glycine | Trizima Base | 1 |
| Chloride | Borate | Trizima Base | 1 |
| Formate | Borate | Trizima Base | 1 |
| Acetate | Borate | Trizima Base | 1 |

When polyacrylamide gels are employed in isoelectric focusing of proteins, rehydration solutions can include, but are not limited to, aqueous ampholytes, aqueous glycerol, and the like. Other solutions which can be used in isoelectric focusing include, but are not limited to, neutral detergents such as polysorbate 20 (Tween ®) 20), Triton ® X (polyoxyethylene ethers) and the like, denaturants such as 6 to 9 molar urea, and charged detergents such as CHAPS (3-[(3-cholamidopropyl)-dimethylammonio]-1 -propanesulfonate) and Zwittergen ® (N-dodecyl-N,N'-dimethyl-3-ammonio-1-propane sulfonate). Any method which is practiced in the art to rehydrate gels horizontally or vertically can be employed in rehydrating the dry polyacrylamide gels of the present invention. For example, one horizontal method is to roll the polyacrylamide gel onto a plate, such as a glass plate rendered hydrophilic, containing a proper volume of solution. Polyacrylamide gels of the present invention also can be rehydrated horizontally by such means as spraying, immersing, or floating the gel face down in the desired solution. Vertical rehydration of polyacrylamide gels can be carried out in gradients of various reagents such as glycerol and other polyols to progressively inhibit the electrophoretic mobility of nucleic acids and proteins as they travel through the gel under the influence of an electrical field.

The rehydration kinetics of the polyacrylamide gels of the present invention are superior to non-treated gels or gels treated with dextran for storage. FIG. 1 shows the rehydration kinetics of five 350$\mu$ thick polyacrylamide gels each bonded to GelBond-Pag ®, heated to 120° C. for one hour. One gel was made without stabilizer, one with dextran as stabilizer, one with sucrose as stabilizer, one with a mixture of sucrose and $\alpha$-methyl-D-glucoside as stabilizer and one with $\alpha$-methyl-D-glucoside as stabilizer. The former two gels curled into tubes on heating and would not uncurl after rehydration. The sucrose-stabilized gel and the gel stabilized with a combination of $\alpha$-methyl-D-glucoside and sucrose did not curl on heating and rehydrated to about 95% or greater of their original weight in 15 minutes. This comparative test demonstrates that for the same gel thickness and total volume, the percent of adsorption is higher in gels stabilized with substituted monosaccharides and/or oligosaccharides than those gels without substituted monosaccharides and/or oligosaccharides or with stabilizers such as dextran. The gel stabilized with $\alpha$-methyl-D-glucoside also did not curl on heating, and rehydrated to about 90% of its original weight in 15 minutes whereas the untreated gel rehydrated to only about 88% of its original weight in 15 minutes. This demonstrates that for the same gel thickness and total volume, the percent adsorption is higher in gels with substituted monosaccharides than those gels that have not been treated.

When the dry polyacrylamide gel comes into contact with rehydration solutions, the absorbent properties of the polyacrylamide cause the matrix to swell, automatically expanding the pores of the gel and allowing the migration of macromolecules through the gel pores in an electric field. The swelling of the pores is controlled by the amount of cross-linking agent in the gel. Less than about 3.1% of cross-linking agent allows the pores to swell to a greater size than when cast, while about 3.5% to about 5% of cross-linking agent allow gel pores to swell only to cast size. Polyacrylamide gels of the present invention can have pore sizes suitable for the high resolution of proteins having molecular weights ranging from about 1200 to about 800,000 daltons and nucleic acid polymers having molecular weights ranging from about 13,000 to about 6,000,000, such as PCR-amplified DNA having from less than 50 to greater than 2,000 base pairs.

In addition, a large pore size gel can be made to behave as a small pore size gel simply by incorporating unsubstituted monosaccharides or small polyols into the gel. These interact with the macromolecules and behave in an analogous manner to reducing the pore size of the gel, but without actually reducing the pore size. The unmodified gel would allow large protein molecules, i.e., greater than about 500,000 daltons, to migrate unrestricted. Conversely, small double-stranded DNA molecules of about 13,000 daltons or less which normally travel with the boundary in MZE can be resolved from DNA of about 3.3 million daltons in the same gel when unsubstituted monosaccharides or small polyols are added. Unsubstituted monosaccharides and polyols can be incorporated into the polyacrylamide gels of the present invention by any suitable means as is practiced in the art. For example, these stabilizers can be added prior to the drying process along with the other stabilizing agents discussed above, or incorporated into the dry polyacrylamide gel as part of the rehydration solution.

Examples of unsubstituted monosaccharides which can be employed to alter the perceived pore size include, but are not limited to, glucose, fructose, mannose and their corresponding sugar alcohols and the like. Examples of suitable small polyols include glycerol and glycols having from about 2 to about 7 carbon atoms. Preferably the glycols have from about 2 to about 3 carbon atoms. Stabilizers such as glycerol reduce the mobility of both proteins and nucleic acids, while unsubstituted monosaccharides reduce the mobility of nucleic acids only. Unsubstituted monosaccharides and polyols are generally incorporated into the polyacrylamide gel in amounts ranging from about 1 to about 50% w/v of the gel or about 0.25 Molar to about 5.0 Molar concentration in the gel.

Other materials also can be incorporated into the polyacrylamide gels, such as detergents, dissociating agents, and denaturants or mixtures thereof. Incorporation of these various reagents will allow performance of specialized electrophoretic separations. For example, polyacrylamide gels allow the separation of dissociated protein in the presence of urea by isoelectric focusing in one dimension followed by separation in the presence or absence of the urea in the second dimension to obtain higher resolution in two-dimensional electrophoresis. Similarly, urea or formamide can be used to maintain DNA in a single-stranded state for DNA sequencing in continuous or discontinuous buffer systems. Examples of other materials which can be used to perform specialized electrophoretic separations include, but are not limited to, zwitter ionic detergents, sodium dodecyl sulfate, polysorbate 20, Triton ® X 100, etc. In conventional gels, detergents, dissociating agents and denaturants must be added prior to polymerization of the gel which can result in interference with polymerization. In accordance with the present invention, these materials are added to the gel during the rehydration step, thus not affecting polymerization.

The polyacrylamide gels of the present invention provide a multipurpose support material. This matrix material can be used for electrophoretic processes in a wide variety of separation procedures, such as isoelectric focusing, conventional continuous zone electrophoresis (CZE) or discontinuous zone electrophoresis (also called multizonal electrophoresis (MZE)), by rehydrating the media with a defined volume of the appropriate buffer or ampholyte. Advantageously, isoelectric focusing of proteins and MZE of nucleic acids can be enhanced through the use of polyacrylamide gels of the present invention.

The process of the present invention produces polyacrylamide gels which can be used as reagent carriers for rapid enzyme visualization with a minimal amount of diffusion. This can be achieved by controlling the reaction product volume and reaction time at elevated temperatures and precisely controlling quantification with appropriate control of monomer concentration and volume during rehydration of the same basic gel matrix. The gel matrix can be rehydrated with various substrates and dye complexes or helper enzymes, and thereafter applied to the surface of the gel on which the electrophoretic separation is carried out. The appropriate reaction then can be carried out at conventional times and temperatures under controlled volumes and an environment limiting diffusion which would otherwise decrease resolution. Due to the protective effect of the gel, enzyme reactions can be carried out at elevated temperatures to speed up the reaction.

In a further embodiment of this invention, monoclonal or polyvalent antibodies can be impregnated into the gel of the present invention. By impregnating such antibodies, one can obtain specific antibody-antigen reactions in both the separating and overlaid gel which can be demonstrated with appropriate stain procedures.

The present invention also produces a polyacrylamide gel which can be used either for in situ DNA hybridization or to transfer DNA to other support media, such as nylon or silicon for hybridization studies or cold isotopic analysis, respectively. Such transfer can be made by placing the gel with separated double-stranded DNA directly on to the second material such that the DNA transfers by passive flow of fluid between the wet and dry supports. No electrophoretic transfer is needed and approximately 80% of the material can be transferred by this technique.

The following examples are supplied to illustrate, but not to limit, the present invention.

EXAMPLE 1

Into a suitable container, 45 grams of acrylamide were added to 90 ml of chloroform heated to 60° C. in a hot water bath. After the acrylamide was dissolved at this temperature, the solution was filtered through Whatman #1 filter paper held in a funnel placed in a heating jacket at 60° C. The filtrate was collected in a Florence flask held at 60° C. After filtration the filtrate was cooled in a water bath to no lower than 22° C. and immediately filtered under vacuum through Whatman #1 filter paper held in a Buchner funnel until all fluid was removed from the crystals. The recrystallized monomer was then removed from the filter paper and dried at ambient temperature in a fume hood.

EXAMPLE 2

To each of three suitable vessels there were added 48 grams of the recrystallized acrylamide prepared as in Example 1. About 1.44 to about 2.4 grams of methylene Bis acrylamide, polyolefinic agarose or piperazine diacrylamide, respectively, and about 100 ml of distilled water were added to the three vessels. The solutions then were heated to about 45° C. to accelerate the dissolution of the monomer and the cross-linker. This provided three stock solutions of about 48% acrylamide monomer and about 3-5% cross-linker.

EXAMPLE 3

Three samples of 50 μl of N,N,N',N'-tetramethylenediamine (TEMED) polymerization accelerator, one volume each of the acrylamide stock solutions of Example 2 and one volume each of 120 mM Tris-sulfate, Tris-chloride or Tris-formate, respectively, at pH 8.9-9.0 were added to each of three separate glass beakers and mixed. To these mixtures were added two volumes (55 mg/100 ml) of ammonium persulfate polymerization catalyst. About 13 ml of each mixture was drawn into separate 20 ml plastic syringes, and degassed by tapping the syringe on the edge of a table until no more bubbles floated to the top of the syringe. The degassed mixtures then were injected along one of the open sides of a casting device. These casting devices consisted of two float-glass plates. Mylar films were affixed to the bottom plates with distilled water to bind the polyacrylamide gel. The upper plates were made hydrophobic by treating two of the upper plates with a solution of 2% dimethyldichlorosilane in 1,1,1-trichloroethane, while the third plate was treated with a solution of acidified ethanol/isopropanol. The distances between the bottom plates affixed with mylar film, and the hydrophobic, upper glass plates were fixed by spacers on each corner of the upper plate to give the desired gel thickness. The sides of each chamber remained open during the polymerization process. Polymerization was completed in about 30 minutes. The polymerized gels then were removed from the chambers and washed several times against distilled water.

EXAMPLE 4

Into each of three suitable dishes or tanks, there was added an aqueous solution of about 5% α-methyl-D-glucoside, an aqueous solution of about 5% sucrose or an aqueous solution of about 5% sucrose and α-methyl-D-glucoside. Each of the three gels prepared in Example 3 then was immersed into one of these three solutions to adsorb the stabilizing substituted monosaccharide and/or oligosaccharide. After the stabilizing agents were absorbed, one impregnated gel was dried at room temperature, the second in a convection oven at about 100° C. and the third in a microwave oven. After the gels were dried, a paper cover was placed on each gel surface, and the gels were packaged. Prior to using the gels, the paper covers were removed from each of the gels. The paper covers were easily removed from each gel without sticking or damage to the gels. Each gel then was rehydrated for about 45 minutes at room temperature in a mixture of 30 mM Tris-formate, with molarity in respect to the formate ion, and 0.5M ribose. The rehydrated gels then were used in multi-zone electrophoresis for the separation of nucleic acids.

While certain representative embodiments and details have been shown for the purpose of illustration of the invention, it will be apparent to those skilled in the art that various changes and modifications can be made therein without departing from the spirit or scope of the invention.

I claim:

1. A process for preparing a stable rehydratable polyacrylamide gel comprising:
   (a) polymerizing acrylamide monomers and one or more cross-linking agents to form a wet polymerized gel in the form of a matrix;
   (b) removing residual components of polymerization from the wet gel;
   (c) incorporating a stabilizing amount of one or more substituted monosaccharides, oligosaccharides, or mixtures thereof within pores of the matrix of the wet gel; and
   (d) drying the wet gel.

2. The process of claim 1, further comprising the step of partially drying the wet gel after removing the residual components of polymerization.

3. The process of claim 1, wherein the substituted monosaccharide is a monosaccharide substituted at the hydroxyl group at carbon 1 with a non-charged group.

4. The process of claim 3, wherein the non-charged group comprises an α-methyl group.

5. The process of claim 4, wherein the substituted monosaccharide comprises α-methyl-D-glucoside or α-methyl-D-mannoside.

6. The process of claim 1, wherein the oligosaccharide has from 2 to 8 repeating monosaccharide units which are the same or different.

7. The process of claim 6, wherein the oligosaccharide comprises sucrose, maltose, lactose, raffinose, melezitose or gentiobiose.

8. The process of claim 1, wherein the substituted monosaccharide or oligosaccharide comprises from about 2% w/v to about 25% w/v of the polyacrylamide gel.

9. The process of claim 1, further comprising incorporating within the pores of the matrix of the polyacrylamide gel a detergent, dissociating agent or denaturant comprised of zwitter ionic detergents, sodium dodecyl sulfate, polysorbate 20, polyoxyethylene ethers, urea or formamide.

10. The process of claim 1, wherein the acrylamide monomer and cross-linking agent are polymerized on a hydrophilic support material.

11. The process of claim 10, wherein the hydrophilic support material comprises polyester sheets, mylar films or glass plates which have been rendered hydrophilic.

12. The process of claim 1, wherein the polyacrylamide gel is in the form of a sheet.

13. The process of claim 12, wherein the sheet has a thickness ranging from about 50 to about 500 microns.

14. A process for preparing a stable rehydratable polyacrylamide gel comprising:
   (a) polymerizing an acrylamide monomer and one or more cross-linking agents on a hydrophilic polyester sheet to form a wet gel matrix;
   (b) removing residual components of polymerization by washing the wet gel with distilled water;
   (c) incorporating a stabilizing amount of α-methyl-D-glucoside or sucrose within the interstices of the wet gel;
   (d) drying the wet gel.

15. A stable rehydratable polyacrylamide gel comprising a matrix of polyacrylamide chains connected by cross-linking material and a stabilizing amount of a substituted monosaccharide or oligosaccharide or mixtures thereof.

16. A stable rehydratable polyacrylamide gel according to claim 15, wherein the substituted monosaccharide is a monosaccharide substituted at the hydroxyl group of carbon 1 with a non-charged group.

17. A stable rehydratable polyacrylamide gel according to claim 16, wherein the non-charged group comprises an α-methyl group.

18. A stable rehydratable polyacrylamide gel of claim 17, wherein the substituted monosaccharide comprises α-methyl-D-glucoside or α-methyl-D-mannoside.

19. A stable rehydratable polyacrylamide gel of claim 15, wherein the oligosaccharide comprises a disaccharide, a trisaccharide or an oligosaccharide having from 4 to 8 repeating units the same or different.

20. A stable rehydratable polyacrylamide gel of claim 19, wherein the oligosaccharide comprises sucrose, lactose, maltose, raffinose, melezitose or gentiobiose.

21. A stable rehydratable polyacrylamide gel of claim 15, wherein the substituted monosaccharide or oligosaccharide comprises from about 2% w/v to about 25% w/v of the gel.

22. A stable ,rehydratable polyacrylamide gel according to claim 15, wherein the gel is in the shape of a sheet, film, cylinder or column.

23. A stable rehydratable polyacrylamide gel according to claim 22, wherein the gel is in the shape of a sheet having a thickness of from about 30 to about 500 microns.

24. A stable rehydratable polyacrylamide gel comprising a matrix comprising polyacrylamide chains connected by one or more cross-linking agents, and a stabilizing amount of α-methyl-D-glucoside or sucrose, wherein the gel is in the shape of a sheet having a thickness of from about 50 to about 500 microns.

25. A stable rehydratable gel according to claim 15 wherein a stabilizing amount of the substituted monosaccharide or oligosaccharide is incorporated into pores of the gel matrix.

26. A rehydratable gel produced by the process of claim 1.

* * * * *

UNITED STATES PATENT AND TRADEMARK OFFICE
CERTIFICATE OF CORRECTION

PATENT NO. : 5,159,049
DATED : October 27, 1992
INVENTOR(S) : Allen

It is certified that error appears in the above-indentified patent and that said Letters Patent is hereby corrected as shown below:

Col. 2, line 34, "intersect" should be --interact--.

Col. 2, line 56, "Electrochoresis" should be --Electrophoresis--.

Signed and Sealed this

Twelfth Day of April, 1994

Attest:

BRUCE LEHMAN

Attesting Officer

Commissioner of Patents and Trademarks